US006988007B1

(12) United States Patent
Morgan et al.

(10) Patent No.: US 6,988,007 B1
(45) Date of Patent: Jan. 17, 2006

(54) SINGLE PASS TELESCOPING CARDIAC LEAD FOR THE LEFT HEART

(75) Inventors: Kevin L. Morgan, Simi Valley, CA (US); Gene A. Bornzin, Simi Valley, CA (US); Joseph J. Florio, La Canada, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 305 days.

(21) Appl. No.: 10/218,353

(22) Filed: Aug. 13, 2002

(51) Int. Cl.
*A61N 1/05* (2006.01)

(52) U.S. Cl. .................. 607/123; 607/125; 600/374

(58) Field of Classification Search ................ 607/122, 607/123, 125, 126; 600/374, 377, 393
See application file for complete search history.

(56) References Cited

U.S. PATENT DOCUMENTS

| | | | | |
|---|---|---|---|---|
| 3,977,411 A | * | 8/1976 | Hughes et al. ................ 607/9 |
| 4,082,893 A | | 4/1978 | Okita ......................... 328/376 |
| 4,271,847 A | | 6/1981 | Stokes ........................ 128/786 |
| 4,289,144 A | | 9/1981 | Gilman ....................... 128/785 |
| 4,332,259 A | | 6/1982 | McCorkle, Jr. ............. 128/786 |
| 4,393,883 A | | 7/1983 | Smyth et al. ............... 128/785 |
| 4,458,677 A | | 7/1984 | McCorkle, Jr. ............. 128/786 |
| 4,479,500 A | | 10/1984 | Smits ......................... 128/786 |
| 4,567,901 A | | 2/1986 | Harris ........................ 128/786 |
| 4,602,645 A | | 7/1986 | Barrington et al. ......... 128/786 |
| 4,643,201 A | | 2/1987 | Stokes ........................ 128/786 |
| 4,664,120 A | | 5/1987 | Hess .......................... 128/642 |
| 4,796,642 A | | 1/1989 | Harris ........................ 129/772 |
| 5,387,233 A | | 2/1995 | Alferness et al. .......... 607/126 |
| 5,411,546 A | | 5/1995 | Bowald et al. ............. 607/126 |
| 5,427,119 A | | 6/1995 | Swartz et al. .............. 128/772 |
| 5,466,252 A | | 11/1995 | Soukup et al. ............. 607/116 |
| 5,476,498 A | | 12/1995 | Ayers ......................... 607/122 |
| 5,487,385 A | | 1/1996 | Avitall ....................... 128/642 |
| 5,497,774 A | | 3/1996 | Swartz et al. .............. 128/658 |
| 5,509,928 A | | 4/1996 | Acken ......................... 607/37 |
| 5,531,781 A | | 7/1996 | Alferness et al. .......... 607/122 |
| 5,545,188 A | | 8/1996 | Bradshaw et al. ........... 607/37 |
| 5,545,204 A | | 8/1996 | Cammilli et al. .......... 607/123 |
| 5,628,779 A | | 5/1997 | Bornzin et al. ............ 607/123 |
| 5,674,274 A | | 10/1997 | Morgan et al. ............ 607/123 |
| 5,683,429 A | | 11/1997 | Mehra ......................... 602/14 |
| 5,683,445 A | | 11/1997 | Swoyer ...................... 607/125 |
| 5,755,766 A | | 5/1998 | Chastain et al. ........... 607/122 |
| 5,824,030 A | | 10/1998 | Yang et al. ................. 607/122 |
| 5,925,073 A | | 7/1999 | Chastain et al. ........... 607/122 |
| 5,964,795 A | | 10/1999 | McVenes et al. ........... 607/122 |

(Continued)

*Primary Examiner*—Kennedy Schaetzle

(57) ABSTRACT

An implantable single-pass cardiac stimulation lead provides for placement of electrodes into electrical contact with two chambers of a patient's heart. The lead includes an inner lead body having at least one electrode at its distal end and an outer lead body having at least one electrode at its distal end. The outer lead body has an internal lumen that slidingly receives the inner lead body. The inner lead body is extendable from the outer lead body at a point proximal to the distal end of the outer lead body. The sliding of the inner lead body relative to the outer lead body enables the inner lead body distal electrode to have a varying distance from the outer lead body distal electrode and enables the inner lead body to extend into the coronary sinus region of the heart to place the inner lead body electrode into electrical contact with the left ventricle.

14 Claims, 4 Drawing Sheets

U.S. PATENT DOCUMENTS

| | | | |
|---|---|---|---|
| 6,021,354 A | 2/2000 | Warman et al. | 607/122 |
| 6,070,104 A | 5/2000 | Hine et al. | 607/123 |
| 6,094,596 A | 7/2000 | Morgan | 607/5 |
| 6,567,704 B2 * | 5/2003 | Sundquist et al. | 607/119 |

* cited by examiner

SINGLE PASS TELESCOPING CARDIAC LEAD FOR THE LEFT HEART

FIELD OF THE INVENTION

The present invention generally relates to an implantable cardiac lead capable of stimulating and sensing in two different chambers of the heart. The present invention is more particularly directed to such a lead implantable in the coronary sinus region of the heart and which has a telescoping configuration to accommodate varying heart sizes and physiology.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. For example, a blood clot released arterially from the left heart, as for example from the left ventricle, could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

Studies have shown that patients suffering from congestive heart failure (CHF) may exhibit marked improvement with left heart pacing. This is attributed to improved cardiac output and decreasing mitral valve regurgitation. These improvements decrease mortality rates and provide the patients with a higher quality of life. Left heart pacing can also improve the condition of patients suffering from left ventricular dysfunction. The preferred pacing configuration for these patients is dual chamber pacing wherein either the right or left atrium is paced along with the left ventricular.

Left heart pacing via the cardiac sinus region can be difficult as stimulation sites vary from patient to patient due to normal anatomical variations. Also, the location and interior size of the vessels and optimal location of the stimulation sites are complicated by an increase in heart size associated with long term CHF. In addition, many patients suffering from CHF have also undergone myocardial infarct(s), bypass surgery, and/or other types of invasive cardiac surgery. Each of these conditions change the position of the vessels within the heart and the position of the stimulation sites.

It is therefore generally thought that left heart pacing requires two separate leads, one lead for placing at least one electrode in either the right atrium or within the coronary sinus adjacent the left atrium and another lead for placing at least one other electrode within the coronary sinus adjacent the left ventricle. However, implanting two such separate leads can be difficult, especially if both leads are to be implanted in the coronary sinus. For example, the implant can be time consuming. Further, there is an inherent risk of interaction between the leads. Moreover, there is an increased risk that one of the leads will become dislodged.

SUMMARY

The invention provides an implantable cardiac stimulation lead suitable for single-pass placement of electrodes into electrical contact with two chambers of a patient's heart. The lead includes a first lead body having a first proximal connector, a first electrode located at a distal end thereof, and a first conductor electrically connected between the first electrode and the first proximal connector. The lead further includes a second lead body having a second proximal connector, a second electrode at a distal end of the second lead body, and a second conductor electrically connected between the second electrode and the second proximal connector. The second lead body has an internal lumen dimensioned such that the first lead body slidably fits within the internal lumen and is extendable from the second lead body at a point proximal to the distal end of the second lead body. The sliding of the first lead body relative to the second lead body enables the first electrode to have a varying distance from the second electrode and enables the first lead body to extend into the coronary sinus region of the patient's heart to place the first electrode into electrical contact with the left ventricle.

Each of the first and second lead bodies may include a stylet lumen and a pre-shaped curved portion for stabilizing the lead bodies within the coronary sinus region when stylets are removed from the stylet lumens. The first lead body may exit the second lead body proximally to the pre-shaped curved portion of the second lead body. Alternatively, the first lead body may exit the second lead body at a peak of the pre-shaped curved portion of the second lead body.

In accordance with further aspects of the present invention, the second lead body may include a bipolar electrode pair including the second electrode and a bipole electrode and cable conductors connecting the electrodes to the second proximal connector. Similarly, the first lead body may include a bipolar electrode pair including the first electrode and a bipole electrode. Here however, the first lead body may include a co-linearly wound multi-filar coil connecting the first lead body bipolar electrodes to the first proximal connector.

In accordance with further aspects of the present invention, each of the first and second lead bodies may be formed of polyurethane insulation. Further, the lumen of the second lead body may include a polytetrafluoroethylene (PTFE) lining.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
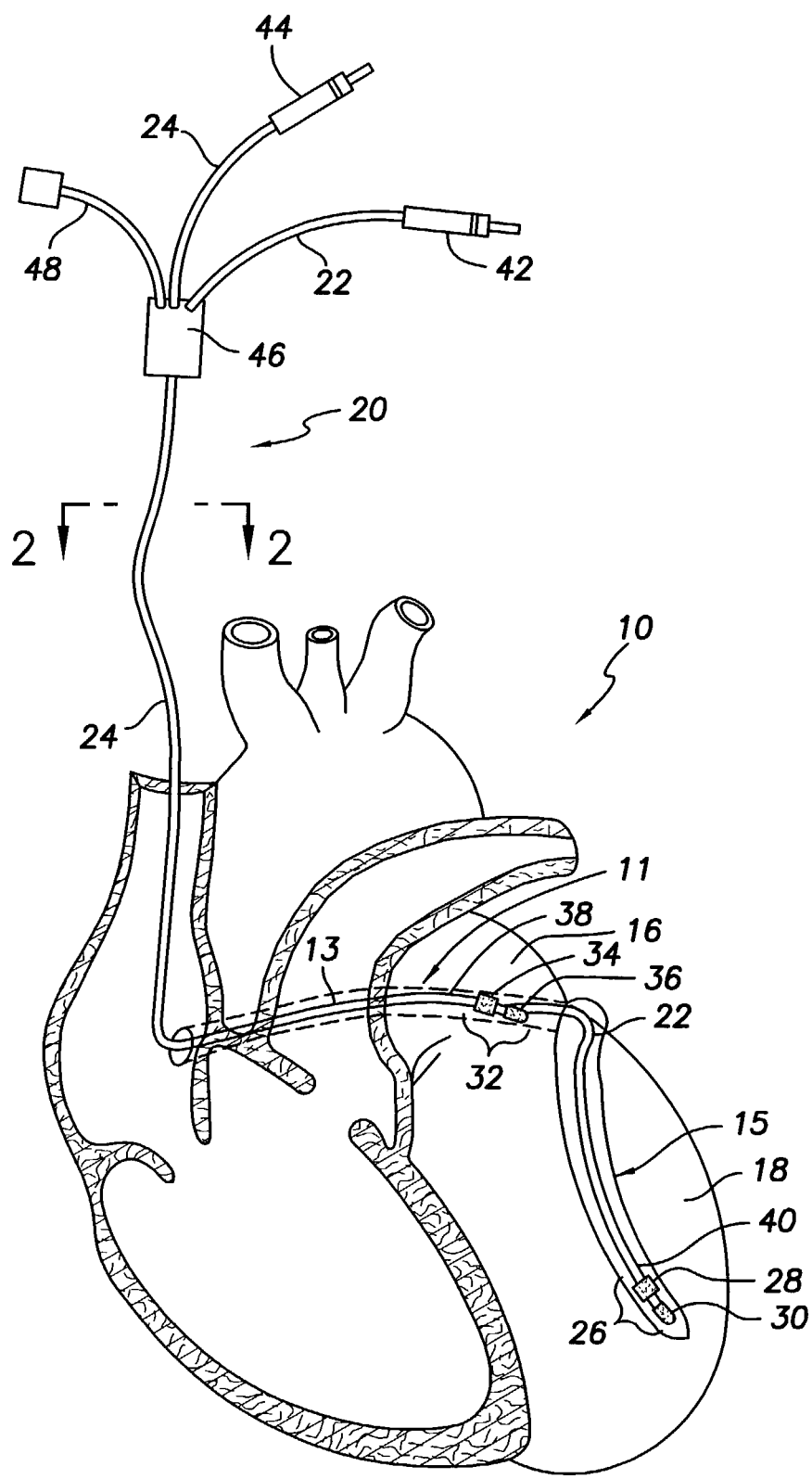
FIG. 1 is a simplified diagram illustrating a single-pass cardiac lead embodying the present invention.

Referring now to FIG. 1, it shows a single-pass cardiac lead 20 embodying the present invention implanted within the coronary veins of the left heart of a heart 10. More specifically, the lead 20 is implanted within the coronary sinus region 11 of the heart 10.

The lead 20 generally includes a first or inner lead body 22 and a second or outer lead body 24. As will be seen subsequently, the inner lead body 22 is slidably and telescopically arranged within the outer lead body. This permits the distal end of the inner lead body 22 to extend distally of the distal end of the outer lead body.

The distal end of the inner lead body carries a bipolar electrode pair 26 including electrodes 28 and 30. Similarly, the distal end of the outer lead body 24 carries a bipolar electrode pair 32 including electrodes 34 and 36. While both lead bodies are shown in the Figures having bipolar electrode pairs, it will be apparent to those skilled in the art that either one or both lead bodies may have unipolar electrodes, as is well known in the art.

As will be noted in FIG. 1, the inner lead body 22 has been slidingly advanced from the outer lead body 24 within the coronary sinus 11 into the great vein 15 adjacent to and into electrical contact with the left ventricle 18. The bipolar electrode pair 32 of the outer lead body 24 is within the coronary sinus 13 adjacent to and in electrical contact with the left atrium 16. With the lead thus configured, both atrial and ventricular pacing and sensing may be carried out from the left side of the heart. Of particular note is the fact that with the inner lead body 22 being slidable within the outer lead body 24, the spacing between the electrode pairs 26 and 32 is variable and selectable to permit each electrode pair to be positioned within the coronary sinus region 11 for optimum sensing and pacing characteristics notwithstanding variations in heart anatomy.

As will be further noted in FIG. 1, the outer lead body 24 further includes a pre-formed arcuate or curved portion 38. The outer lead body 24 assumes the arcuate or curved shape of portion 38 when a stylet (not shown) of the type well known in the art is removed from a stylet lumen within the outer lead body. The stylet lumen will be described subsequently with reference to FIG. 2. The pre-shaped arcuate portion 38 serves to stabilize the outer lead body 24 within the coronary sinus 13 of the coronary sinus region 11.

As may further be noted in FIG. 1, the inner lead body 22 exits, and hence is extendable from, the outer lead body 24 at a point proximal to the distal end of the outer lead body. It has been found that locating the exit port for the inner lead body at a point proximal to the end of the outer lead body disposes the distal tip of the inner lead body in a direction which is more likely to avoid encountering a vein sidewall when the inner lead body is advanced from the outer lead body. This makes it easier to advance the inner lead body to its desired position within the coronary sinus region. In accordance with this embodiment, the inner lead body 22 exits the outer lead body at a point 37 proximal to the pre-shaped arcuate portion 38 of the outer lead body.

The inner lead body 22 also includes a pre-formed arcuate or curved portion 40. The inner lead body 22 assumes the arcuate or curved shape of portion 40 when a stylet (not shown) is similarly removed from a stylet lumen within the inner lead body. The pre-shaped arcuate or curved portion 40 similarly serves to stabilize the inner lead body 22 within the coronary vein 15 of the coronary sinus region 11.

With further reference to FIG. 1, the lead 20 further includes a first proximal connector 42 and a second proximal connector 44. The first proximal connector 42 is connected to the electrode pair 26 of the inner lead body 22 by a first pair of conductors to be described subsequently with reference to FIG. 2. The second proximal connector 44 is connected to the electrode pair 32 of the outer lead body 24 by a second pair of conductors to be described subsequently with reference to FIG. 2.

The connectors 42 and 44 are accommodated on lead 20 by a junction 46 of the type known in the art. The junction further carries a flush port 48 which communicates with an internal lumen of the outer lead body 24 within which the inner lead body 22 is slidingly arranged. The flush port 48 permits a lubricant, such as saline, to be administered to the internal lumen to lubricate the internal lumen and inner lead body 22. This permits easier movement of the inner lead body 22 with respect to the outer lead body 24 due to a reduced sliding force.

Figure 2:
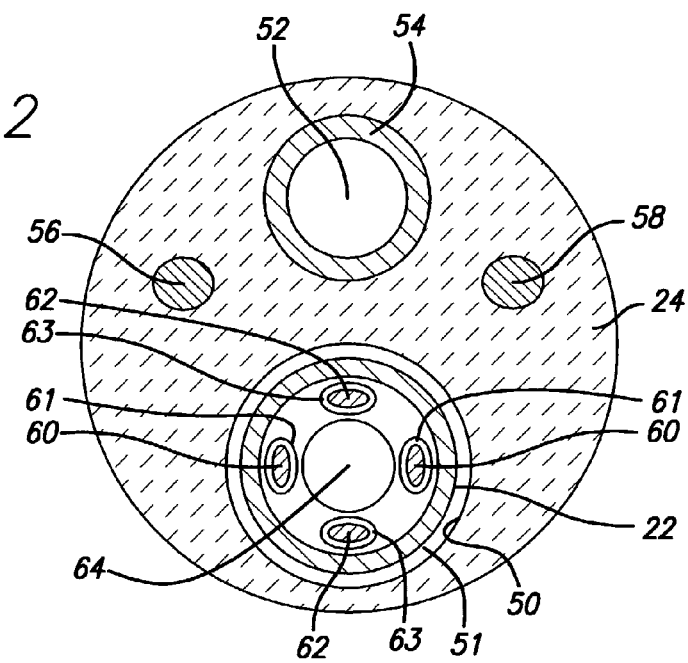
FIG. 2 is a cross-sectional view taken across lines 2—2 of FIG. 1.

FIG. 2 shows a cross section of the outer lead body 24 with the inner lead body 22 slidingly arranged therein. The outer lead body 24 and the inner lead body 22 are preferably formed of polyurethane insulation such as Pellethane 2363-55D. This particular insulation material allows for smaller lead cross-sections, better strength, and better surface lubriciousness. However, other insulation materials known in the art may also be used to form the outer and inner lead bodies.

The inner lead body 22 is slidingly received within the internal lumen 50 of the outer lead body 24. The flush port 48 (FIG. 1) communicates with the space 51 between the inner lead body 22 and the inner wall of the internal lumen 50 to permit the sliding arrangement of the inner and outer lead bodies to be lubricated.

To accommodate the previously mentioned outer lead body stylet, the outer lead body 24 includes a stylet lumen 52. The stylet lumen 52 is preferably lined with a tube liner 54 of polytetrafluoroethylene (PTFE) or other suitable material such as ethyltetrafluoroethylene (ETFE).

As previously mentioned, a pair of conductors connect the electrode pair 32 of the outer lead body to the second proximal connector 44. In accordance with this preferred embodiment, those conductors take the form of cable conductors 56 and 58. Other forms of conductors as are known in the art may also be employed.

To accommodate the other previously mentioned stylet for the inner lead body, the inner lead body includes a stylet lumen 64 formed by the inner surface of multi-filar coil wires 60 and 62. The multi-filar coil wires 60 and 62 form the aforementioned first pair of conductors which couple the electrode pair 26 to the first proximal connector 42. In accordance with this preferred embodiment, the wires 60 and 62 include an insulation 61 and 63 respectively which may be, for example, PTFE or ETFE.

Figure 3:
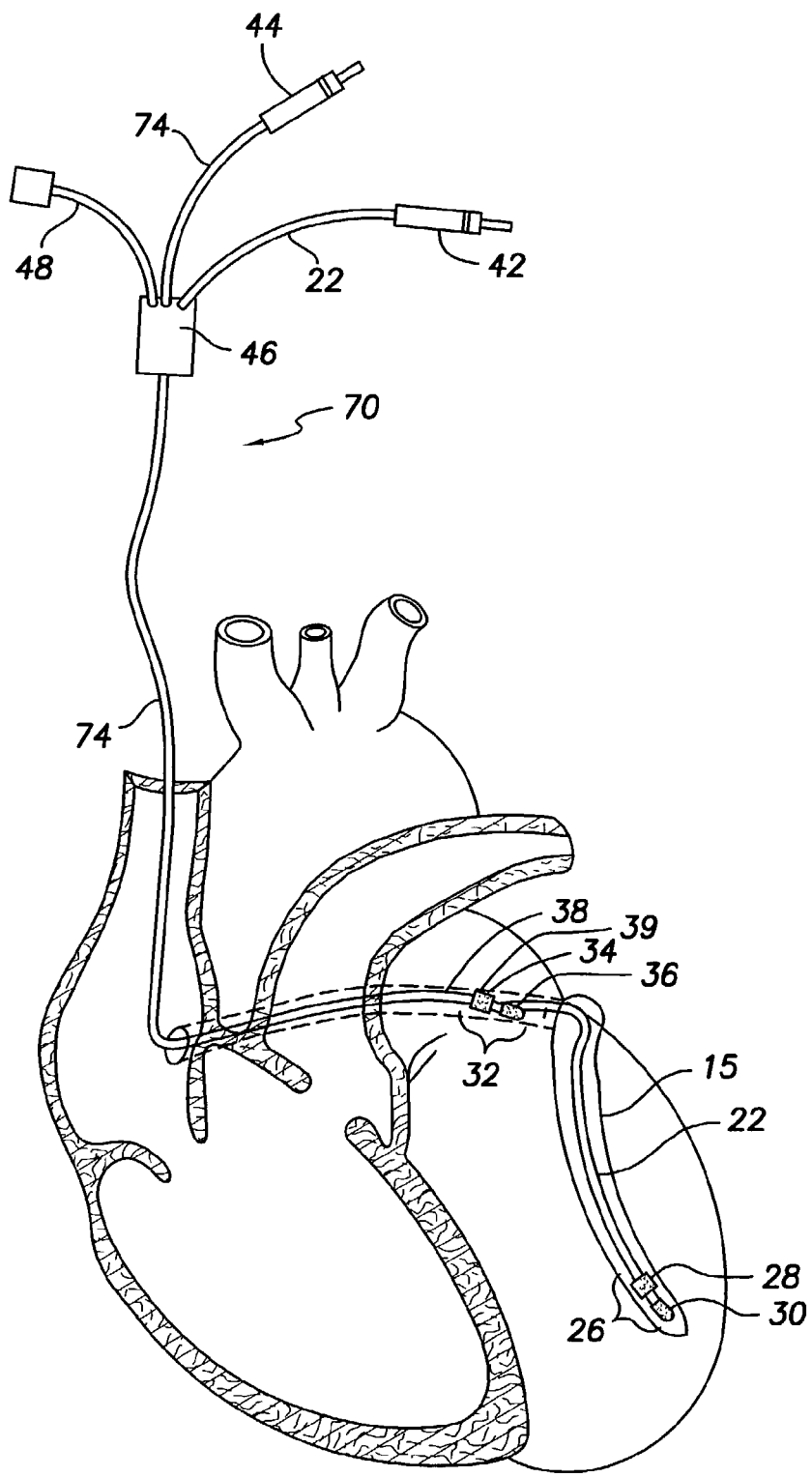
FIG. 3 is another simplified diagram illustrating a further single-pass cardiac lead embodying the present invention.

FIG. 3 shows another single-pass lead 70 embodying the present invention. The lead 70 is identical to the lead 20 of FIG. 1 except that the outer lead body 74 is arranged to permit the inner lead body 22 to exit at the peak 39 of the pre-shaped arcuate portion 38. This configuration may serve to assist the extension of the inner lead body 22 into the great vein 15 in the heart of some patients.

Figure 4:
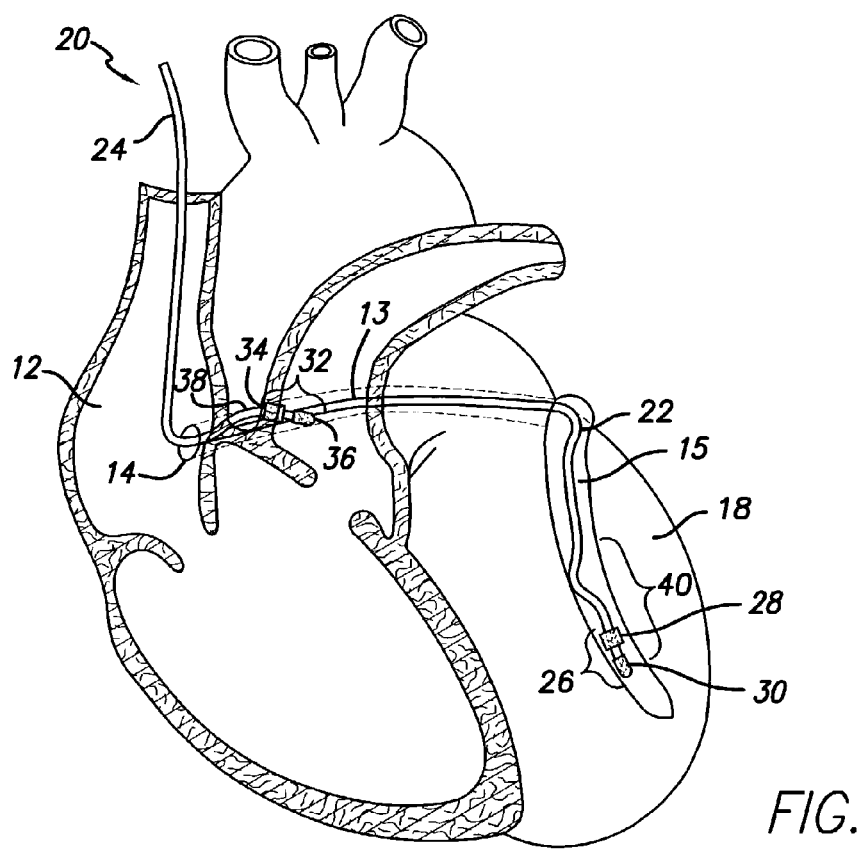
FIG. 4 shows the lead of FIG. 1 configured for pacing the right atrium and the left ventricle.

FIG. 4 shows the lead 20 of FIG. 1 configured for pacing the right atrium and the left ventricle. Here it may be seen that the pre-shaped arcuate portion 38 resides just in or distally to the coronary sinus ostium 14. This places the bipolar electrode pair 32 in electrical contact with the right atrium to permit right atrial pacing. The pre-shaped arcuate portion 38 stabilizes the outer lead body 24 within the coronary sinus 13.

The inner lead body 22 has been extended into the great vein 15 of the coronary sinus region. Here it may also be seen that the pre-shaped arcuate portion 40 is more pronounced for stabilizing the inner lead body 22 within the great vein 15 (or other appropriate coronary vein). The bipolar electrode pair 26 is placed toward the apex of the heart in electrical contact with the left ventricle to permit left ventricular pacing.

Figure 5:
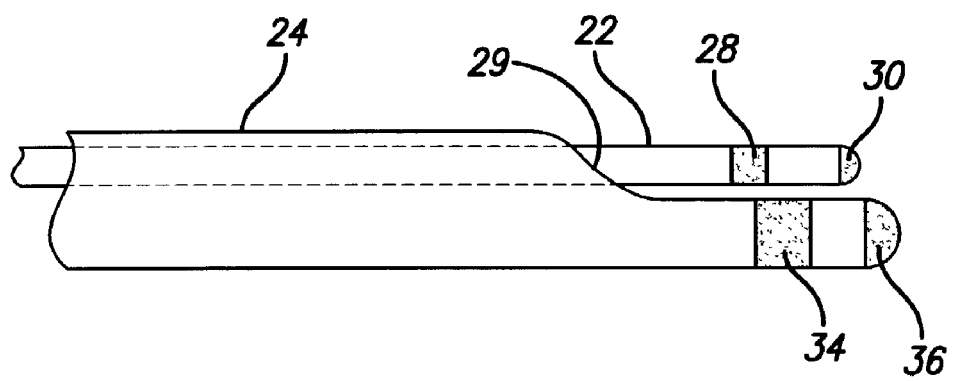
FIG. 5 shows an exit port in the outer lead body from which the inner lead body exits the outer lead body.

With respect to each of the embodiments illustrated in FIGS. 1, 3 and 4, the distal electrode 36 of the bipolar electrode pair 32 is located at or immediately adjacent the distal end of the outer lead body 24. The bipole or proximal electrode 34 of the bipolar electrode pair 32 may be spaced from the distal electrode 36 by a distance between 1 and 30 millimeters and preferably 5 millimeters. As shown in FIG. 5, the inner lead body 22 exits the outer lead body 24 proximal of electrode 34, and the exit port 29 is about 1 to 10 centimeters, and preferably about 4 to 5 centimeters, from the distal end of lead body 24. In an alternate embodiment, the exit port 29 is located between electrode 34 and electrode 36. In any event, the exit port 29 is positioned so that it is relatively close to the distal end of outer lead body 24 to permit both outer lead body 24 and inner lead body 22 to be placed in the coronary sinus. In this manner, the outer lead body 24 may be sufficiently advanced through the coronary sinus so that the exit port 29 is disposed within the coronary sinus. Once the exit port is located in the coronary sinus, the inner lead body 22 may be deployed from the exit port 29 and into the coronary sinus, for further advancement within the coronary sinus.

While the invention has been described by means of specific embodiments and applications thereof, it is understood the numerous modifications and variations could be made thereto by those skilled in the art without departing from the spirit and scope of the invention. For instance, the disclosed features, either singularly or in groups, could be used with other leads to advantageous results. It is therefore to be understood that within the scope of the claims, the invention may be practices otherwise than as specifically described herein.

What is claimed is:

1. An implantable cardiac stimulation lead suitable for single-pass placement of electrodes into electrical contact with two chambers of a patient's heart, the lead comprising:
   a first lead body having a first proximal connector, a first tip electrode located at a distal end thereof, and a first conductor electrically connected between the first tip electrode and the first proximal connector; and
   a second lead body having a second proximal connector, a second tip electrode at a distal end of the second lead body, and a second conductor electrically connected between the second tip electrode and the second proximal connector, the second lead body having an internal lumen dimensioned such that the first lead body slidably fits within the internal lumen and is extendable from the second lead body at an exit port, the exit port disposed at a point spaced from and proximally adjacent to the distal end of the second lead body to permit the exit port, the first tip electrode, and the second tip electrode to be positioned in the coronary sinus region;
   wherein the sliding of the first lead body relative to the second lead body enables the first tip electrode to have a varying distance from the second tip electrode and enables the first lead body to extend into the coronary sinus region of the patient's heart to place the first tip electrode into electrical contact with the left ventricle and the second tip electrode into electrical contact with the atria; and
   wherein the second tip electrode has a continuous surface without an opening.

2. The cardiac lead of claim 1 wherein each of the first and second lead bodies includes a stylet lumen.

3. The cardiac lead of claim 1 wherein the distal end of the second lead body includes a pre-shaped arcuate portion and wherein the first lead body exits the second lead body proximally to the pre-shaped arcuate portion of the second lead body.

4. The cardiac lead of claim 1 wherein the distal end of the second lead body includes a pre-shaped arcuate portion, wherein the pre-shaped arcuate portion of the second lead body includes a peak and wherein the first lead body exits the second lead body at the peak of the pre-shaped arcuate portion of the second lead body.

5. The cardiac lead of claim 1 wherein the distal end of the second lead body includes a pre-shaped arcuate portion that stabilizes the distal end of the second lead body within the coronary sinus region.

6. The cardiac lead of claim 1 wherein the second lead body includes a bipolar electrode pair including the second tip electrode and a bipole electrode, wherein the second conductor is a first cable conductor connected between the second electrode and the second proximal connector, wherein the second lead body further includes a second cable conductor connected between the bipole electrode and the second proximal connector, and wherein the bipole electrode is a ring electrode.

7. The cardiac lead of claim 1 wherein the first lead body includes a bipolar electrode pair including the first tip electrode and a bipole electrode, wherein the first lead body includes a co-linearly wound multi-filar coil including the first conductor and a third conductor, wherein the third conductor is connected between the bipole electrode and the first proximal connector, and wherein the bipole electrode is a ring electrode.

8. The cardiac lead of claim 1 wherein each of the first and second lead bodies is formed of polyurethane insulation.

9. The cardiac lead of claim 1 wherein the lumen of the second lead body includes a tetrafluoroethylene lining.

10. The cardiac lead of claim 1 wherein the second lead body includes a bipolar electrode pair including the second tip electrode and a bipole electrode, wherein the second tip electrode and bipole electrode are spaced apart on the second lead by a spacing of between one and thirty millimeters, and wherein the bipole electrode is a ring electrode.

11. The cardiac lead of claim 10 wherein the spacing is five millimeters.

12. The cardiac lead of claim 1 wherein the first lead body includes a stylet lumen and a pre-shaped distal portion that stabilizes the first lead within the coronary sinus region after a stylet is removed from the stylet lumen and wherein the pre-shaped distal portion is proximal to the first tip electrode.

13. The cardiac lead of claim 12 wherein the pre-shaped distal portion has a pre-shaped curvature.

14. A cardiac lead for implant in the coronary sinus region of a heart, the lead comprising:

an outer lead body having a proximal connector, a lumen, a distal end, a tip electrode at the distal end of the outer lead body that is placeable in electrical contact with one of the right atrium and the left atrium within the coronary sinus region, and a conductor electrically coupling the tip electrode to the outer lead body proximal connector; and an inner lead body having a proximal connector, a distal end, a tip electrode at the distal end of the inner lead body and a conductor electrically coupling the tip electrode to the inner lead body proximal connector, the inner lead body being telescopically disposed within the lumen of the outer lead body and slidingly extendable distally from the outer lead body at an exit port, the exit port disposed at a point spaced from and proximally adjacent to the distal end of the outer lead body to permit the exit port, the tip electrode of the outer lead body, and the tip electrode of the inner lead body to be positioned in the coronary sinus region, the tip electrode of the inner lead body being placeable in electrical contact with the left ventricle within the coronary sinus region, and the tip electrode of the outer lead body having a continuous surface without an opening.

\* \* \* \* \*